United States Patent

Wagner

Patent Number: 5,304,179
Date of Patent: Apr. 19, 1994

[54] SYSTEM AND METHOD FOR INSTALLING A SPINAL FIXATION SYSTEM AT VARIABLE ANGLES

[75] Inventor: Erik J. Wagner, Allen, Tex.
[73] Assignee: AMEI Technologies Inc., Wilmington, Del.
[21] Appl. No.: 79,150
[22] Filed: Jun. 17, 1993
[51] Int. Cl.$^5$ .............................................. A61B 17/56
[52] U.S. Cl. ...................................... 606/61; 403/371
[58] Field of Search .................... 606/61, 59, 105, 90, 606/53, 72, 57, 58, 87, 55; 403/365, 367, 371, 400, 390, 395

[56] References Cited

U.S. PATENT DOCUMENTS

| | | | |
|---|---|---|---|
| 4,386,603 | 6/1983 | Mayfield | 606/105 |
| 4,763,644 | 8/1988 | Webb . | |
| 4,805,602 | 2/1989 | Puno et al. . | |
| 4,887,596 | 12/1989 | Sherman | 606/61 |
| 4,950,269 | 8/1990 | Gaines | 606/61 |
| 5,129,388 | 7/1992 | Vignaud et al. | 606/61 |
| 5,176,679 | 1/1993 | Lin | 606/61 |

OTHER PUBLICATIONS

B. E. Fredrickson, et al., "1992 Volvo Award in Experimental Studies, Vertebral Burst Fractures: An Experimental, Morphologic and Radiographic Study", *Spine*, vol. 17, No. 9, 1992, pp. 1012–1021.

Primary Examiner—Tamara L. Graysay
Attorney, Agent, or Firm—Baker & Botts

[57] ABSTRACT

A spinal fixation system is provided for installing spinal instrumentation (18) posterior to a patient's spine to fuse selected vertebrae. The spinal fixation system (10) includes a plurality of connectors (12) and associated bushings (16). The connectors (12) comprise a first portion (20) canted at an angle of 7.5° relative to a second portion (22). The connectors (12) secure the spinal instrumentation (18) to the pedicle screws (14). Each bushing (16) contains an angled borehole (28). The combination of the angles produced by the connectors (12) and the borehole (28) of each of the bushings (16) allows the installation of pedicle screws (14) at various angles relative to the patient's spine.

21 Claims, 3 Drawing Sheets

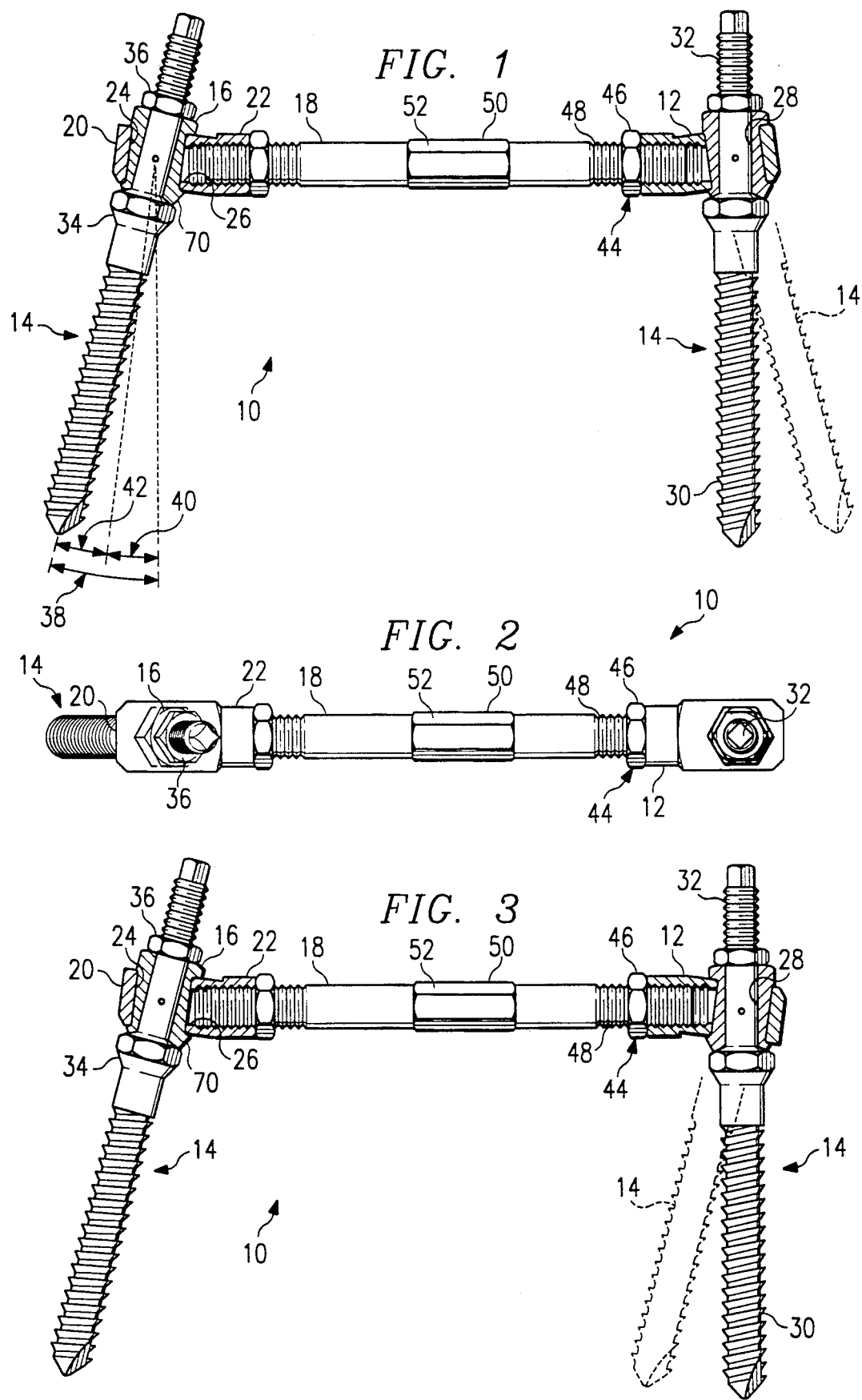

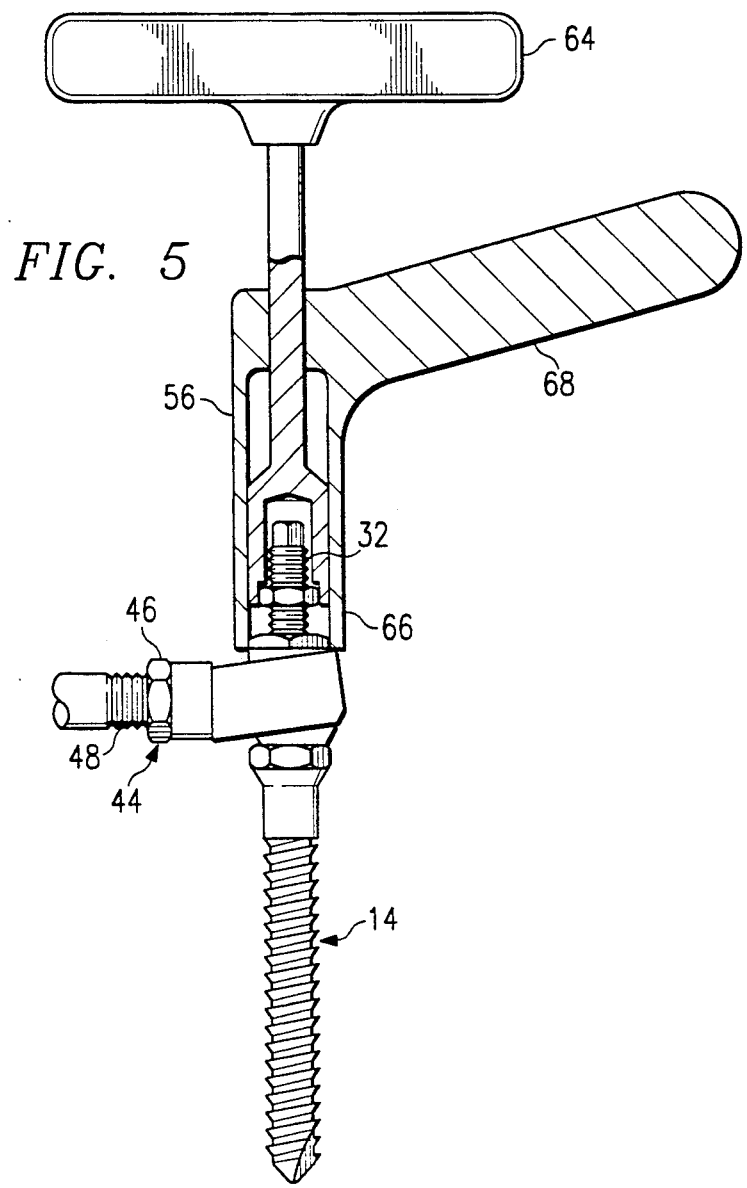
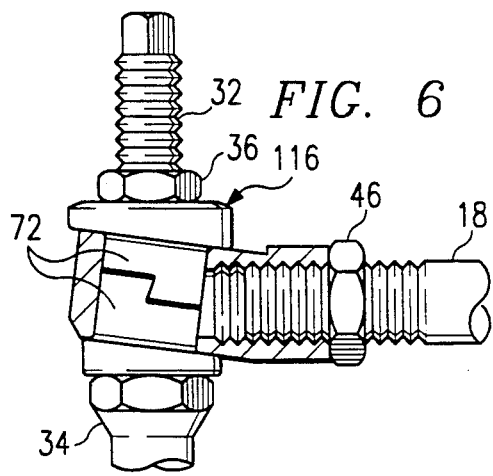
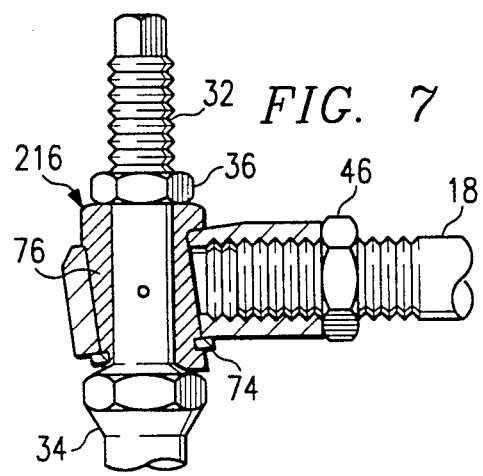

SYSTEM AND METHOD FOR INSTALLING A SPINAL FIXATION SYSTEM AT VARIABLE ANGLES

TECHNICAL FIELD OF THE INVENTION

This invention relates in general to the field of surgically implanted devices, and more particularly relates to a system and method for installing a spinal fixation system at variable angles.

BACKGROUND OF THE INVENTION

Spinal fixation, such as lumbar sacral fusion and the correction of spinal deformities such as scoliotic curves, is a well known and frequently used medical procedure. Pedicle, lateral, and oblique mounting means may be used to secure corrective spinal instrumentation to a portion of the spine that has been selected to be fused by arthrodesis.

A spinal fixation system comprises corrective spinal instrumentation that is attached to selected vertebrae of the spine by screws, hooks, and clamps. The corrective spinal instrumentation comprises spinal rods or plates, which are generally parallel to the patient's back. The corrective spinal instrumentation further comprises connecting rods, which extend from the spinal rods or plates. Spinal fixation systems are used to correct problems in the lumbar and thoracic portions of the spine, and are often installed posterior to the spine on opposite sides of the spinous process and adjacent to the transverse process.

Various types of screws, hooks, and clamps have been used for attaching corrective spinal instrumentation to selected portions of a patient's spine. Examples of pedicle screws and other types of attachments are shown in U.S. Pat. Nos. 4,763,644; 4,805,602; 4,887,596; 4,950,269; and 5,129,388. These patents are incorporated by reference for all purposes within this application.

Spinal fixation systems often require that the connecting rods be maintained at a certain fixed angle with the spinal rods or plates that make up the corrective spinal instrumentation. The spinal rods or plates that comprise the corrective spinal instrumentation are often generally parallel to the patient's back. The angle that each connecting rod makes with the attached vertebra may change only slightly during treatment. Additionally, the angle that a connecting rod makes with a vertebra may vary from person to person due to the unique anatomical structure of each patient. As a result, prior devices tend to comprise blocks and screws produced with various unchangeable angles to enable a physician to couple the corrective spinal instrumentation to the connecting rods while accommodating the initial placement of the connecting rods with the patient's vertebra. Therefore, large sets of components may be necessary to accommodate the many significant anatomical variations from person to person.

Some prior devices may accommodate a limited number of different placements of the connecting rods in the patient's vertebrae. Yet these devices often require a different set of components for each of the specified angles. In addition, such prior devices are often limited to fixed angles in increments of five degrees, such as 0°, 5°, and 10°.

SUMMARY OF THE INVENTION

In accordance with the present invention, a spinal fixation system is provided which substantially eliminates or reduces the disadvantages and problems associated with prior spinal fixation systems. The present invention provides a spinal fixation system with a plurality of connectors. Each connector has a body with a first opening extending radially therethrough and a second opening extending at least partially therethrough. The first opening is formed at an angle relative to the second opening.

The spinal fixation system further comprises a bushing sized to be received within the first opening of the connector. The bushing comprises a bore extending longitudinally therethrough. The bore in the bushing is disposed at an angle relative to the first opening in the connector. A pedicle screw is inserted through the bore of the bushing. A fastening assembly is provided for engaging the second opening of the connector to the spinal instrumentation.

A technical advantage of the present invention is that a single bushing and a single connector may be used to install a pedicle screw at various angles relative to a patient's spine. By using rotatable bushings, each having bores disposed at an angle relative to the first opening of the connector, a connector can accommodate pedicle screws that are inserted at various angles relative to a patient's spine. The components of the system can be adjusted by physicians to achieve the necessary configuration relative to a patient's spine without necessitating the interchanging of components.

Another technical advantage of the present invention includes a spinal fixation system that is not limited to a certain number of fixed, immutable angles, but can be adjusted to provide any angle within the range of the spinal fixation system.

A further technical advantage of the present invention includes minimizing the number of different components required for a spinal fixation system to accommodate different patients. By minimizing the number of components, the level of technological expertise needed to properly install the system is reduced and the cost of inventory is minimized.

BRIEF DESCRIPTION OF THE DRAWINGS

For a more complete understanding of the present invention and the advantages thereof, reference is now made to the following description taken in conjunction with the accompanying drawings in which like reference numbers indicate like features and wherein:

FIG. 1 is a side view partially in section and partially in elevation of one embodiment of a spinal fixation system constructed according to teachings of the present invention;

FIG. 2 is a top view of the spinal fixation system of FIG. 1;

FIG. 3 is a side view partially in section and partially in elevation of another embodiment of a spinal fixation system constructed according to the teachings of the present invention;

FIG. 5 is a side view partially in section and partially in elevation with portions broken away of a handling tool for manipulating a spinal fixation system constructed according to the teachings of the present invention;

FIG. 6 is a side view partially in section and partially in elevation with portions broken away of a bushing constructed according to the teachings of the present invention; and FIG. 7 is a side view partially in section and partially in elevation with portions broken away of a bushing constructed according to the teachings of the present invention.

DETAILED DESCRIPTION OF THE INVENTION

Figure 4:
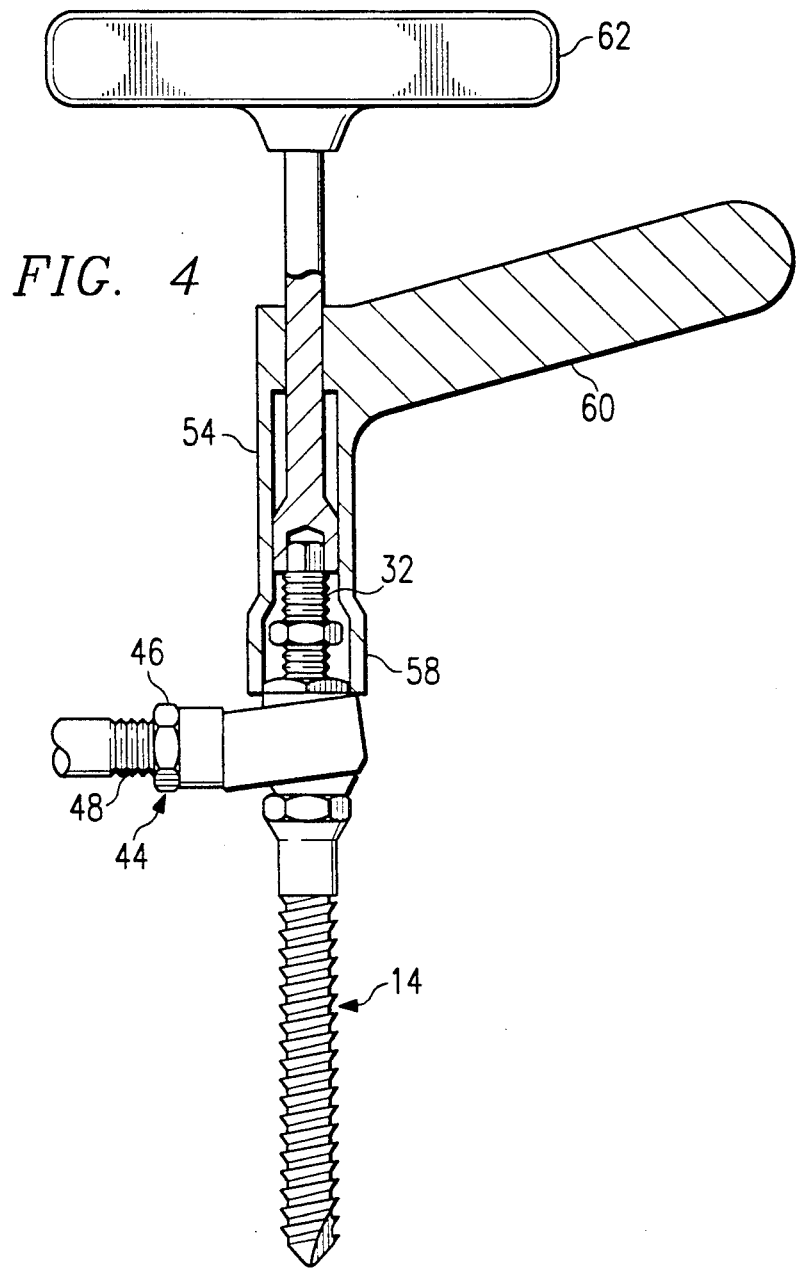
FIG. 4 is a side view partially in section and partially in elevation of a handling tool for manipulating a spinal fixation system constructed according to the teachings of the present invention.

The preferred embodiments of the present invention and its advantages can best be understood by referring to FIGS. 1 through 7 of the drawings, like numerals being used for like and corresponding parts of the various drawings.

FIG. 1 shows a spinal fixation system indicated generally at 10 and constructed according to the teachings of the present invention. Spinal fixation system 10 comprises connectors 12, pedicle screws 14, cam bushings 16, and spinal instrumentation 18. Connectors 12 comprise a first portion 20 and a second portion 22. First portion 20 of connector 12 has a first opening 24, which extends through connector 12. Second portion 22 of connector 12 has a second opening 26, which extends partly through second portion 22 and is arranged longitudinally relative to second portion 22 of connector 12. First portion 20 of connector 12 is canted at an angle of 7.5° relative to second portion 22.

First opening 24 of each connector 12 is adapted to receive a single cam bushing 16. Each cam bushing 16 contains a borehole 28. Each cam bushing 16 can be rotated 360° in first opening 24. When cam bushing 16 is arranged at a setting of 0° of rotation in first opening 24, borehole 28 is disposed at an angle relative to a central axis of first opening 24. By rotating cam bushing 16 in first opening 24, the angle of borehole 28 relative to the central axis of first opening 24 changes. At a predetermined point of rotation of cam bushing 16 in first opening 24, borehole 28 is aligned with the central axis of first opening 24 of connector 12. Once the rotation of cam bushing 16 in first opening 24 passes the point at which borehole 28 is aligned with the central axis of first opening 24, borehole 28 is again disposed at an angle relative to the central axis of first opening 24 of connector 12.

In one embodiment of cam bushing 16, particular positions along the rotational path of cam bushing 16 correspond to an exact angular relationship between borehole 28 and the central axis of first opening 24 of connector 12. For example, at a setting of 0° of rotation of cam bushing 16 in first opening 24, borehole 28 is disposed at an angle of 7.5° relative to the central axis of first opening 24. Rotation of cam bushing 16 to a position of 90° or 270° from the 0° setting in first opening 24 results in alignment of borehole 28 with the central axis of first opening 24. At a setting of 180° of rotation of cam bushing 16 from the 0° setting in first opening 24, borehole 28 is disposed at an angle of −7.5° relative to the central axis of first opening 24.

A pedicle screw 14 extends through borehole 28 of each of cam bushings 16. Pedicle screws 14 may be attached to selected vertebrae of the patient. Pedicle screw 14 comprises a first threaded portion 30, and a second threaded portion 32. First threaded portion 30 is operable to couple pedicle screw 14 to the individual vertebra. A shoulder 34 is disposed on first threaded portion 30 of each pedicle screw 14. Shoulder 34 is operable to positively engage cam bushing 16. A lock nut 36 is coupled to second threaded portion 32 to assist in securing cam bushing 16 on pedicle screw 14. FIG. 2 shows a top view of spinal fixation system 10 of FIG. 1 from second threaded portions 32 of pedicle screws 14.

Spinal instrumentation 18 may comprise, for example, a spinal rod, or a plate. The angle between the longitudinal axis of each pedicle screw 14 and a plane perpendicular to spinal instrumentation 18 is known as a pedicle screw angle, indicated generally at 38. Pedicle screw angle 38 is produced by the addition of a connector angle, indicated generally at 40, and a cam bushing angle, indicated generally at 42. Connector angle 40 is the angle between the central axis of first opening 24 and the plane perpendicular to spinal instrumentation 18. Cam bushing angle 42 is the angle between borehole 28 of cam bushing 16 and the central axis of first opening 24. In one embodiment, connector angle 40 comprises 7.5°. However, first portion 20 and second portion 22 of connector 12 could be canted at other appropriate angles as required for specific spinal fixation systems.

Pedicle screw angle 38 is considered to be a positive angle if first threaded portion 30 is angled away from spinal instrumentation 18. Pedicle screws 14 in FIG. 1 have positive pedicle screw angles 38. Pedicle screw angle 38 is considered to be a negative angle if first threaded portion 30 is angled toward spinal instrumentation 18. The superimposed pedicle screw 14 in FIG. 3 has a negative pedicle screw angle. similarly, connector angle 40 and cam bushing angle 42 are considered to be positive angles if they are angled away from the center of spinal instrumentation 18. Connector angle 40 and cam bushing angle 42 are considered to be negative angles if they are angled toward the center of spinal instrumentation 18. However, unlike connector angle 40 and pedicle screw angle 38, cam bushing angle 42 is measured with respect to the central axis of first opening 24.

As stated above, cam bushing angle 42 is the angle formed by the central axis of first opening 24 and borehole 28. If borehole 28 is aligned with the central axis of first opening 24, cam bushing angle 42 is 0°. However, if borehole 28 is not aligned with the central axis of first opening 24, cam bushing angle 42 will either subtract from or add to connector angle 40. In one embodiment, cam bushing angle 42 may range from −7.5° to 7.5°. When cam bushing 16 is at a position of 0° of rotation in first opening 24, cam bushing angle 42 is −7.5°. As cam bushing 16 is rotated in first opening 24, cam bushing angle 42 remains negative until cam bushing 16 reaches a predetermined point of rotation in which borehole 28 is aligned with the central axis of first opening 24. At this point cam bushing angle 42 is 0°. Continued rotation of cam bushing 16 in first opening 24 produces a positive cam bushing angle 42. When cam bushing 16 is at a point of 180° of rotation in first opening 24, cam bushing angle 42 is 7.5°. By implementing the teachings of the present invention, cam bushing 16 may be designed to produce other appropriate ranges of cam bushing angles 42.

If cam bushing 16 is at a position of 0° of rotation in first opening 24, borehole 28 is aligned with the plane perpendicular to spinal instrumentation 18, resulting in cam bushing angle 42 of −7.5°. The addition of cam bushing angle 42 of −7.5° to existing connector angle 40 of 7.5° yields pedicle screw angle 38 of 0°. If cam bushing 16 is at a position of rotation of 180° in first opening 24, the angle formed by borehole 28 and the central axis of first opening 24 is 7.5° when measured relative to the central axis of first opening 24. Thus, the addition of cam bushing angle 42 of 7.5° to existing connector angle 40 of 7.5° yields a pedicle screw angle 38 of 15° relative to the plane perpendicular to spinal instrumentation 18.

As was discussed earlier, cam bushing 16 can rotate 360° in first opening 24. When cam bushing 16 is at an approximate position of rotation of 90° or 270° in first opening 24, borehole 28 is aligned with the central axis of first opening 24, producing cam bushing angle 42 of 0°. The connector angle 40 is 7.5°. The combination of these two angles yields a pedicle screw angle 38 of 7.5°. Thus when borehole 28 of cam bushing 16 is aligned with first opening 24 of connector 12, pedicle screw angle 38 is the same as connector angle 40. The range of possible pedicle screw angles 38 is demonstrated by the superimposed pedicle screw 14 in FIG. 1.

Pedicle screw angles 38 in, the range of 0° to −15° may also be produced. This is done by inverting connector 12, as shown in FIG. 3, so that second portion 22 of connector 12 is canted toward the vertebrae of the patient. As a result, pedicle screw 14 is angled toward the center of spinal instrumentation 18. Connector angle 40 is fixed at −7.5°. Thus, when cam bushing 16 is at a first position of rotation of 0°, cam bushing angle 42 is 7.5°. The combination of connector angle 40 and this cam bushing angle 42 results in a pedicle screw angle 38 of 0°. When cam bushing 16 is at a position of 180° of rotation in first opening 24, cam bushing angle 42 is −7.5°. The combination of connector angle 40 and this cam bushing angle 42 results in a pedicle screw angle 38 of −15°. The range of possible negative pedicle screw angles is demonstrated by the superimposed pedicle screw 14 in FIG. 3. Therefore, the embodiment in FIG. 1 can yield any pedicle screw angle in the range of 15° to −15°. By implementing the teachings of the present invention, cam bushings 16 and connectors 12 may be designed to produce other appropriate ranges of pedicle screw angles 38.

Spinal instrumentation 18 is coupled between two connectors 12 by way of a fastening assembly indicated generally at 44. Fastening assembly 44 in FIG. 1 comprises a bolt 46. Both ends 48 of spinal instrumentation 18 may be threaded. However, the threads on each end 48 have opposite directions of pitch. The middle section of spinal instrumentation 18 may comprise a turnbuckle 50. Turnbuckle 50 comprises flat surfaces 52 formed on a portion of spinal instrumentation 18 larger than the diameter of the remainder of spinal instrumentation 18.

As a result of the opposing directions of pitch of the threads on each of ends 48 of spinal instrumentation 18, rotating turnbuckle 50 causes pedicle screws 14 to move relative to each other. If turnbuckle 50 is rotated in one direction, pedicle screws 14 move toward each other along the threads of spinal instrumentation 18. If turnbuckle 50 is rotated in the opposite direction, pedicle screws 14 move away from each other along the threads of spinal instrumentation 18. Pedicle screw angles 38 remain constant when pedicle screws 14 are moved by way of the rotation of turnbuckle 50.

As discussed above, each cam bushing 16 can be rotated 360° in first opening 24. FIG. 4 shows a cam bushing handling tool 54 that is used for rotating cam bushing 16. FIG. 5 shows a lock nut handling tool 56 that is used for positioning lock nut 36 on second threaded portion 32 of pedicle screw 14. To rotate cam bushing 16, lock nut 36 may need to be loosened. The cam bushing handling tool 54 has an outer concentric cylinder 58 that fits over pedicle screw 14 and engages cam bushing 16. Outer concentric cylinder 58 can be manipulated by an L-handled wrench 60. Within outer concentric cylinder 58 is a T-handled wrench 62 that engages pedicle screw 14. During the rotation of cam bushing 16 by L-handled wrench 60, T-handled wrench 62 is used to hold pedicle screw 14 to insure that pedicle screw 14 does not move during the rotation of cam bushing 16. T-handled wrench 62 may also be used to prevent pedicle screws 14 from moving during the tightening of associated lock nuts 36.

Lock nut handling tool 56 can be used to secure lock nut 36 to cam bushing 16. Lock nut handling tool 56 is similar in design to cam bushing handling tool 54. A T-handled handled wrench 64 is used to engage lock nut 36. Outer concentric cylinder 66 of L-handled wrench 68 is used to engage cam bushing 16. T-handled wrench 64 is rotated relative to L-handled wrench 68 to secure lock nut 36 to cam bushing 16.

A number of methods are disclosed for securing cam bushing 16 in connector 12. In the embodiment of FIG. 1, cam bushing 16 is secured to connector 12 by flaring one end 70 of cam bushing 16 around the edges of second opening 26 of connector 12. In the embodiment of FIG. 6, cam bushing 116 comprises two interlocking pieces 72. Each of the pieces 72 overlaps the edge of connector 12. Each piece 72 further has a matching lip that allows the pieces to snap together in the interior of the first opening 24 of connector 12. In the embodiment shown in FIG. 7, cam bushing 216 comprises a snap ring 74 and a body 76. When cam bushing 216 is placed through first opening 24 of connector 12, snap ring 74 snaps into place over the edges of second portion 22 of connector 12. Thereby, snap ring 74 securely holds cam bushing 216 in place in first opening 24. Depression of snap ring 74 allows the removal of cam bushing 216 from connector 12. Other suitable embodiments may be used to secure cam bushing 16 to connector 12.

Prior to beginning the surgical procedure, the physician determines the degree of angular correction that is needed for each of pedicle screws 14. One embodiment uses two connectors 12, two pedicle screws 14, two cam bushings 16, and spinal instrumentation 18. Additional combinations of pedicle screws 14 and spinal rods 18 could also be used, along with the attendant increase in the number of cam bushings 16 and connectors 12 needed.

First, pedicle screws 14 are installed in the selected vertebrae, and shoulders 34 are threaded on pedicle screws 14. The remainder of the spinal fixation system 10 is placed on pedicle screws 14 to accommodate the initial angle of insertion of pedicle screws 14 into the vertebrae of the patient. In one embodiment, spinal fixation system 10 is fastened to pedicle screws 14 so that spinal instrumentation 18 is substantially parallel with the patient's back. Cam bushings 16 are placed in connectors 12, which are coupled to opposite ends 48 of spinal instrumentation 18. If the physician seeks to attach connectors 12 to positive pedicle screw angles 38, connectors 12 are angled away from the vertebrae. Negative pedicle screw angles 38 are accommodated by angling connector 12 toward the vertebrae, as is demonstrated by connector 12 in FIG. 3.

Second, cam bushings 16 are rotated so that the combination of cam bushing angle 42 and connector angle 40 allows cam bushings 16 to fit over pedicle screws 14. Thus, cam bushing 16 is rotated to allow spinal fixation system 10 to fit over existing pedicle screws 14 while allowing spinal instrumentation 18 to be substantially parallel with the patient's back.

Third, fine adjustments may be made to cam bushings 16 to assure a correct fit with the established pedicle screw angle 38. As discussed above, cam bushing handling tool 54 is used to rotate a particular cam bushing 16 while holding the associated pedicle screw 14 in place. Lock nut handling tool 56 is used to secure lock nuts 36 to each cam bushing 16 while holding pedicle screws 14 in place. The rotation of cam bushing 16 can be manipulated in the manner described above to adjust the angle of insertion of pedicle screw 14 into the patient's vertebrae.

Finally, turnbuckle 50 can be rotated to move pedicle screws 14 relative to each other. For example, a first pedicle screw 14 may be attached to one of the upper vertebrae, and a second pedicle screw 14 may be attached to one of the lower vertebrae. Turnbuckle 50 can be rotated such that the first and second pedicle screws 14 are moved away from each other along the threads of spinal instrumentation 18, resulting in the distraction of the vertebrae attached to pedicle screws 14. In addition, rotating turnbuckle 50 in the opposite direction moves pedicle screws 14 towards each other along the threads of spinal instrumentation 18, resulting in a compression of the attached vertebrae.

Although the present invention has been described in detail, it should be understood that various changes, substitutions and alterations can be made herein without departing from the spirit and the scope of the inventions as defined in the following claims.

What is claimed is:

1. A spinal fixation system for fusing selected portions of a patient's spine comprising:
   an instrumentation;
   a plurality of connectors for attaching the instrumentation to the selected portions of the patient's spine;
   each connector having a body with a first opening extending radially therethrough and a second opening extending at least partially therethrough;
   the first opening having an axis formed at an angle relative to an axis of the second opening;
   a bushing within the first opening and having a bore extending longitudinally therethrough;
   the bore having an axis disposed at an angle relative to the first opening axis;
   a pedicle screw within the bore of the bushing; and
   a fastening assembly engaging the second opening of the connector with the instrumentation.

2. A spinal fixation system as defined in claim 1 wherein the instrumentation further comprises an elongated member having threads on each end in engagement with the second opening of a pair of said connectors.

3. The spinal fixation system as defined in claim 1 wherein the instrumentation further comprises a spinal rod.

4. The spinal fixation system as defined in claim 1 wherein the pedicle screw further comprises:
   a first shoulder on the exterior of the pedicle screw intermediate the ends thereof;
   a first threaded portion extending from the first shoulder in one direction; and
   a second threaded portion extending from the first shoulder in the opposite direction.

5. The spinal fixation system as defined in claim 4 wherein said second threaded portion is received within the bore of the bushing.

6. The spinal fixation system as defined in claim 2 further comprising an enlarged portion on the exterior of the instrumentation intermediate the ends thereof.

7. The spinal fixation system as defined in claim 1 wherein the instrumentation further comprises:
   a spinal rod with a plurality of threads formed on each end of the spinal rod;
   flat surfaces on the exterior of the spinal rod intermediate the ends thereof; and
   the threads on the ends of the spinal rod in engagement with the second opening in a pair of said connectors.

8. The spinal fixation system as defined in claim 1 further comprising:
   each body having a first portion and a second portion;
   the first opening extending through the first body portion; and
   the second opening extending only partially through the second body portion.

9. The spinal fixation system as defined in claim 1 wherein each bushing further comprises retainer ring for releasably securing each bushing within its respective first opening.

10. A spinal fixation system for posterior installation to fuse selected portions of a patient's spine comprising:
    a rigid instrumentation;
    a plurality of connectors for attachment of the rigid instrumentation to selected vertebrae of the patient's spine;
    each connector having a body with a first opening with an axis extending radially therethrough and a second opening extending at least partially through the body;
    the first opening having an axis formed at an angle relative to an axis of the second opening;
    a bushing having a bore with an axis extending longitudinally therethrough and the bushing received within the first opening;
    the axis of the first opening disposed at an angle relative to the axis of the bore in the bushing;
    a pedicle screw received within the bore of the bushing; and
    a fastening assembly engaging the second opening of each connector with the rigid instrumentation.

11. A spinal fixation system as defined in claim 10 wherein the rigid instrumentation further comprises an elongated member having threads on each end in engagement with matching threads formed in the second opening of a pair of said connectors.

12. The spinal fixation system as defined in claim 10 wherein the rigid instrumentation further comprises a spinal rod.

13. The spinal fixation system as defined in claim 10 wherein the pedicle screw further comprises:
    a first shoulder on the exterior of the pedicle screw intermediate the ends thereof;
    a first threaded portion for engagement with one of the selected vertebrae extending from the first shoulder in one direction; and
    a second threaded portion extending from the first shoulder in the opposite direction.

14. The spinal fixation system as defined in claim 13 further comprising:
    the second threaded portion is received within the bore of the bushing; and a lock nut engaging the second threaded portion to secure the connector to the pedicle screw.

15. The spinal fixation system as defined in claim 11 further comprising an enlarged portion on the exterior of the rigid instrumentation intermediate the ends thereof for engagement by a surgical tool to rotate the rigid instrumentation relative to the pair of said connectors.

16. The spinal fixation system as defined in claim 10 wherein the rigid instrumentation further comprises:
    a spinal rod with a plurality of threads formed on each end of the spinal rod;
    flat surfaces on the exterior of the spinal rod intermediate the ends thereof; and
    the threads on each end of the spinal rod in engagement with the second opening in one of said connector and the threads on each end of the spinal rod having opposite directions of pitch whereby rotation of the spinal rod results in movement of the pedicle screws relative to each other.

17. The spinal fixation system as defined in claim 10 further comprising:
    each body having a first portion and a second portion;
    the first opening extending through the first body portion;
    the second opening extending only partially through the second body portion; and
    the first portion disposed at an angle relative to the second portion.

18. The spinal fixation system as defined in claim 10 wherein each bushing further comprises a retainer ring for releasably securing the bushing within its respective first opening.

19. The spinal fixation system as defined in claim 10 wherein each bushing further comprises interlocking pieces for securing the bushing within its respective first opening.

20. A method for assembling a spinal fixation system for installing instrumentation for fusing selected portions of a patient's spine, comprising the steps of:
    providing a plurality of connectors, the connectors having a first opening extending radially therethrough and a second opening extending at least partially therethrough, with the first opening having an axis formed at an angle relative to an axis of the second opening;
    providing a plurality of bushings having bores extending longitudinally therethrough, each bore having an axis;
    placing the bushings within the first openings of the plurality of connectors, with the axis of the bores of the bushings disposed at an angle relative to the axis of the first openings of the plurality of connectors;
    providing an instrumentation;
    coupling the second openings of the connectors to the instrumentation;
    rotating the bushings to achieve a desired angle of each of the bores relative to the instrumentation; and
    coupling a plurality of bores to the bushings proximate the bores of the bushings.

21. The method of claim 20, wherein the instrumentation further comprises a spinal rod and wherein the step of coupling the second openings of the connectors to the instrumentation further comprises the step of coupling the spinal rod between the second openings of the connectors, with the spinal rod having a plurality of threads on each end of the spinal rod, and with the threads having opposite directions of pitch whereby rotation of the spinal rod results in movement of the pedicle screws relative to each other.

* * * * *